United States Patent
Benson et al.

(10) Patent No.: US 12,002,556 B2
(45) Date of Patent: Jun. 4, 2024

(54) PRE-OPERATIVE ASSESSMENT AND INVENTORY MANAGEMENT SYSTEM

(71) Applicant: Warsaw Orthopedic, Inc., Warsaw, IN (US)

(72) Inventors: Nicholas Benson, Collierville, TN (US); Rodney R. Ballard, Lakeland, TN (US)

(73) Assignee: WARSAW ORTHOPEDIC, INC., Warsaw, IN (US)

( * ) Notice: Subject to any disclaimer, the term of this patent is extended or adjusted under 35 U.S.C. 154(b) by 158 days.

(21) Appl. No.: 17/474,139

(22) Filed: Sep. 14, 2021

(65) Prior Publication Data

US 2021/0407636 A1 Dec. 30, 2021

Related U.S. Application Data

(63) Continuation of application No. 16/043,986, filed on Jul. 24, 2018, now Pat. No. 11,158,405, and a
(Continued)

(51) Int. Cl.
*G16H 30/20* (2018.01)
*A61B 34/10* (2016.01)
(Continued)

(52) U.S. Cl.
CPC ............ *G16H 10/60* (2018.01); *A61B 34/10* (2016.02); *G16H 30/20* (2018.01); *G16H 80/00* (2018.01); *A61B 2034/108* (2016.02)

(58) Field of Classification Search
CPC ......... G16H 40/20; G16H 50/20; G16H 40/40
See application file for complete search history.

(56) References Cited

U.S. PATENT DOCUMENTS

| 6,306,087 B1 | 10/2001 | Barnhill et al. |
| 2003/0004652 A1 | 1/2003 | Brunner et al. |

(Continued)

FOREIGN PATENT DOCUMENTS

| WO | WO-2007009263 A1 * | 1/2007 | ........... G06Q 10/087 |
| WO | WO-2013158521 A1 * | 10/2013 | ............. A61B 17/00 |

OTHER PUBLICATIONS

Lin, Ji-Tzuoh, et al. "Development of capacitive pure bending strain sensor for wireless spinal fusion monitoring." Sensors and Actuators A: Physical 138.2 (2007): 276-287. (Year: 2007).*

(Continued)

*Primary Examiner* — Jason B Dunham
*Assistant Examiner* — Constantine Siozopoulos
(74) *Attorney, Agent, or Firm* — FOX ROTHSCHILD LLP (57) ABSTRACT

A system of generating a pre-operative assessment of a patient includes an assessment system configured to communicate with client electronic devices. The system receives patient information pertaining to a patient, uses the patient information to access one or more medical images associated with the patient, performs one or more image processing techniques on the one or more medical images to identify measurements pertaining to an internal bodily structure of the patient, identifies one or more implant components for the patient, determines whether the one or more implant components are currently stocked, in response to determining that the one or more implant components are not currently stocked, automatically generates and placing an order for the one or more implant components that are not stocked, generates a pre-operative assessment for the patient, and causes the assessment to be displayed on a display device of a client electronic device.

16 Claims, 5 Drawing Sheets

Related U.S. Application Data continuation-in-part of application No. 16/043,928, filed on Jul. 24, 2018, now Pat. No. 11,141,115.

(51) Int. Cl.
*G16H 10/60* (2018.01)
*G16H 40/40* (2018.01)
*G16H 80/00* (2018.01)

(56) References Cited

U.S. PATENT DOCUMENTS

| | | |
|---|---|---|
| 2003/0215122 A1 | 11/2003 | Tanaka |
| 2005/0010445 A1 | 1/2005 | Krishnan et al. |
| 2005/0049497 A1 | 3/2005 | Krishnan et al. |
| 2006/0242159 A1 | 10/2006 | Bishop et al. |
| 2007/0047794 A1 | 3/2007 | Lang et al. |
| 2011/0092804 A1 | 4/2011 | Schoenefeld et al. |
| 2011/0213221 A1* | 9/2011 | Roche .................. A61B 5/4504 600/301 |
| 2011/0319745 A1 | 12/2011 | Frey |
| 2013/0282399 A1 | 10/2013 | Ware et al. |
| 2014/0081659 A1 | 3/2014 | Nawana et al. |
| 2016/0117817 A1* | 4/2016 | Seel ........................ G06T 7/337 382/131 |
| 2016/0220174 A1 | 8/2016 | Yip et al. |
| 2016/0270927 A1 | 9/2016 | Zellmer et al. |
| 2016/0361121 A1 | 12/2016 | Reicher et al. |
| 2017/0007420 A1 | 1/2017 | Stevenson et al. |
| 2017/0061375 A1* | 3/2017 | Laster .................... G16H 50/30 |
| 2018/0303552 A1 | 10/2018 | Ryan et al. |

OTHER PUBLICATIONS

European Search Report in Application No. 19841733.9 dated Mar. 22, 2022.

\* cited by examiner

| SPINE TUMOR DASHBOARD | ADD A NEW PATIENT | CANCEL |

SYSTEMIC DISEASE:

ECOG. ⓘ (CLICK FOR REFERENCE MATERIAL)   [0] [1] [2] [3] [4] [5]

DOES THE PATIENT HAVE DIABETES?   [YES] [NO]

IS THE PATIENT A SMOKER?   [YES] [NO]

CARDIO STRESS TEST:   [____]

PULMONARY FUNCTION:   [____]

LIVER FUNCTION:   [NORMAL] [ABNORMAL]

PLATELET COUNT (ENTER NUMBER):   [____]

BONE DENSITY (ENTER T-SCORE NUMBER):   [____]

SURGEON NOTES (ENTER NOTES IMPORTANT FOR PATIENT ASSESSMENT):   [____]

PREPARED BY:   [____]

[SAVE PATIENT]
[CANCEL]

PRE-OPERATIVE ASSESSMENT AND INVENTORY MANAGEMENT SYSTEM

CROSS-REFERENCE TO RELATED U.S. PATENT APPLICATIONS

This Application is a Continuation Application of U.S. Non-provisional patent application Ser. No. 16/043,986, entitled "Pre-Operative Assessment and Inventory Management System", filed Jul. 24, 2018, and a Continuation-in-Part of U.S. Non-provisional patent application Ser. No. 16/043,928, entitled "Pre-Operative Assessment System", filed Jul. 24, 2018, which are both incorporated herein by reference in their entirety.

TECHNICAL FIELD

The present disclosure generally relates to a system that utilizes information from a variety of sources to provide a pre-operative assessment of a patient.

BACKGROUND

Currently, the process of performing a pre-operative assessment for a patient can be tedious and time consuming. This is because the relevant resources necessary for such an assessment are usually disjointed, incomplete or difficult to access or interpret.

SUMMARY

In an embodiment, a system of generating a pre-operative assessment of a patient includes an assessment system configured to communicate with one or more client electronic devices via a communication network. The assessment system includes one or more computing devices and a computer-readable storage medium. The computer-readable storage medium includes one or more programming instructions that, when executed, cause the one or more computing devices to receive patient information pertaining to a patient, use at least a portion of the patient information to access one or more medical images associated with the patient, perform one or more image processing techniques on the one or more medical images to identify, from the one or more medical images, one or more measurements pertaining to an internal bodily structure of the patient, identify, based on the one or more measurements, one or more implant components for the patient, determine whether the one or more implant components are currently stocked, in response to determining that the one or more implant components are not currently stocked, automatically generate and placing an order for the one or more implant components that are not stocked, and generate a pre-operative assessment for the patient, wherein the pre-operative assessment includes: an indication of the one or more implant components, and for each of the one or more implant components, an indication of whether the implant components are currently stocked. The system causes the assessment to be displayed on a display device of a client electronic device.

In an embodiment, the system may receive information pertaining to movement of the patient that was obtained from one or more sensors positioned on a portion of the patient's body. The system may receive patient information from a client electronic device. Optionally, the system may receive one or more medical images from one or more of the following: electronic medical record data; or electronic health record data.

The system may perform one or more image processing techniques on the one or more medical images to identify a condition associated with the patient by causing the one or more computing devices to apply a machine learning model that has been trained on a set of bodily structures.

The system may identify one or more implant components for the patient by accessing a component data store, where the component data store comprises dimensional information pertaining to one or more implant components, searching the component data store for one or more implant components having dimensional information that corresponds to the one or more measurements, and identifying a unique identifier associated with each implant component having dimensional information that corresponds to the one or more measurements.

In an embodiment, the system may cause the one or more computing devices to determine whether the one or more implant components are currently stocked by searching an inventory data store for one or more of the unique identifiers, and determining an inventory status associated with the one or more unique identifiers.

DETAILED DESCRIPTION

In some embodiments, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior". Generally, similar spatial references of different aspects or components indicate similar spatial orientation and/or positioning, i.e., that each "first end" is situated on or directed towards the same end of the device. Further, the use of various spatial terminology herein should not be interpreted to limit the various insertion techniques or orientations of the implant relative to the positions in the spine.

The following terms shall have, for purposes of this application, the respective meanings set forth below:

A "computing device", "electronic device", or "computer" refers a device or system that includes a processor and memory. Each device may have its own processor and/or memory, or the processor and/or memory may be shared with other devices as in a virtual machine or container arrangement. The memory will contain or receive programming instructions that, when executed by the processor, cause the electronic device to perform one or more operations according to the programming instructions. Examples of electronic devices include personal computers, servers, mainframes, virtual machines, containers, mobile electronic devices such as smartphones, Internet-connected wearables, tablet computers, laptop computers, and appliances and other devices that can communicate in an Internet-of-things arrangement. In a client-server arrangement, the client device and the server are electronic devices, in which the server contains instructions and/or data that the client device accesses via one or more communications links in one or more communications networks. In a virtual machine arrangement, a server may be an electronic device, and each virtual machine or container also may be considered an electronic device. In the discussion below, a client device, server device, virtual machine or container may be referred to simply as a "device" for brevity. Additional elements that may be included in electronic devices will be discussed below in the context of FIG. 5.

The terms "memory," "computer-readable medium" and "data store" each refer to a non-transitory device on which computer-readable data, programming instructions or both are stored. Unless the context specifically states that a single device is required or that multiple devices are required, the terms "memory," "computer-readable medium" and "data store" include both the singular and plural embodiments, as well as portions of such devices such as memory sectors.

Figure 1:
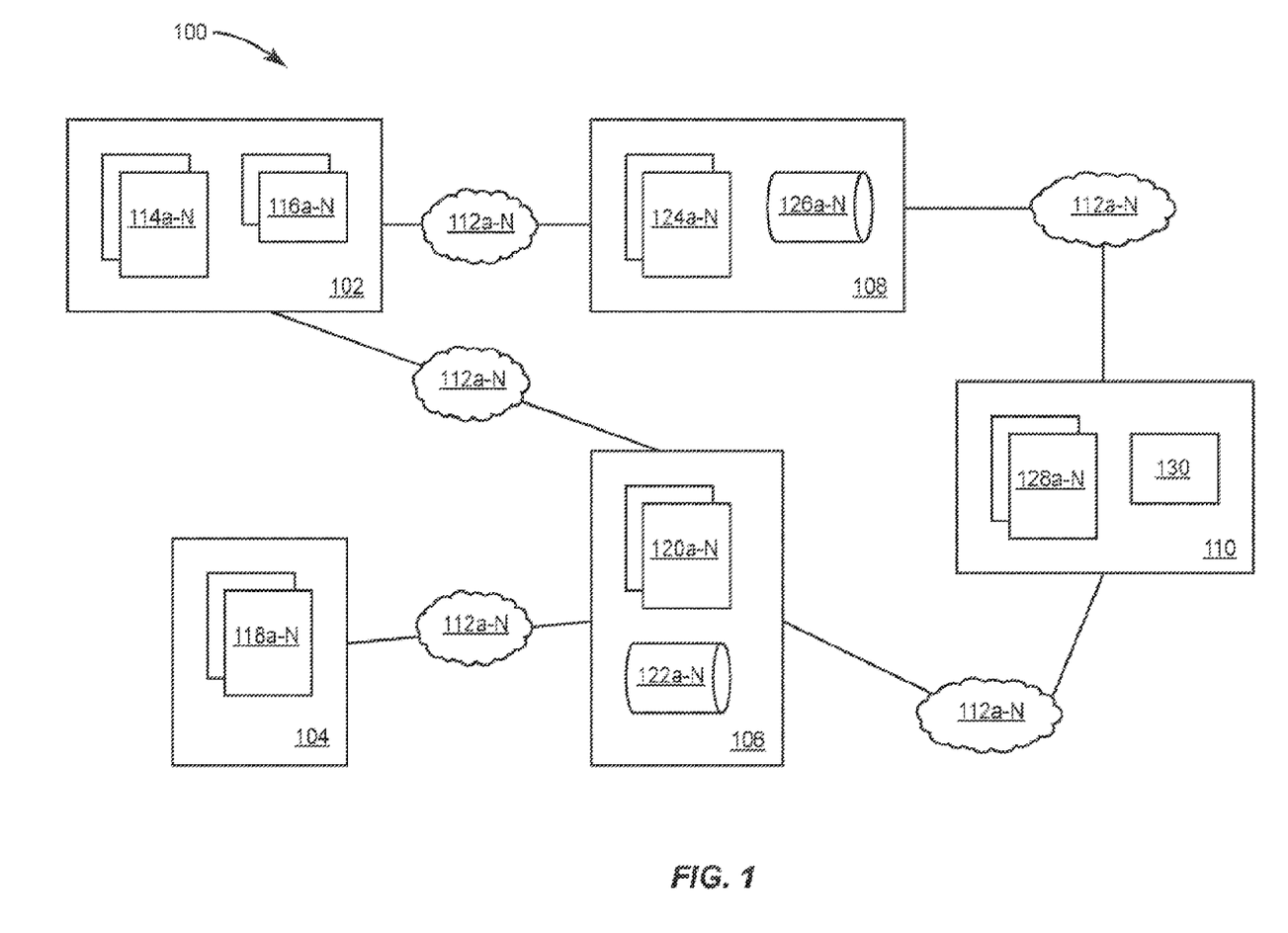
FIG. 1 illustrates an example assessment system according to an embodiment.

FIG. 1 illustrates an example assessment system according to an embodiment. As illustrated in FIG. 1, an assessment system 100 may include client system 102, a surgeon system 104, an analytics system 106, a hospital record system 108 and/or an operating room system 110. A client system 102 may include one or more client electronic devices 114a-N. In an embodiment, a client electronic device 114a-N may be an electronic device used to receive input associated with a patient. A client electronic device 114a-N may belong to a patient. For instance, a client electronic device 114a-N may be a smartphone, tablet, mobile device, or computer belonging to a patient. Alternatively, a client electronic device 114a-N may be an electronic device used by a patient or other to provide input concerning the patient and the patient's condition. For instance, a patient in a clinical setting may be given access to a tablet to provide answers or feedback. As another example, a clinician may use a client electronic device 114a-N to provide such input.

In an embodiment, a client system 102, may include one or more sensors 116a-N. Sensors 116a-N may be used to gather information about a patient. Example sensors include, without limitation, inertial measurement units (IMUs), electrocardiogram (ECG) sensors, electromyography (EMG) sensors, accelerometers, altimeters, thermometers, microphones, cameras, barometers and/or the like. In an embodiment, a sensor may be at least a portion of an implant, such as a spinal implant. For instance, a load sensing assembly for a spinal implant may communicate with an electronic device (such as a reader device) using near field communication or via another communication means. A reader device may obtain information from the implant over this communication channel. Such devices may include, for example, the systems disclosed in U.S. patent application Ser. No. 16/039,592 entitled Load Sensing Assembly for a Spinal implant, incorporated herein by reference.

A surgeon system 104 may include one or more provider electronic devices 118a-N. A provider electronic device 118a-N may include, for example, a smartphone, tablet, mobile device, laptop computer, desktop computer and/or the like. In an embodiment, a surgeon or other healthcare provider may use a provider electronic device 118a-N to access and view patient information.

In an embodiment, an analytics system 106 may include one or more electronic devices 120a-N and/or data stores 122a-N. The one or more electronic devices may be servers. An analytics system 106 may store patient information and sensor information received from a client system 102. As explained in more detail below, an analytics system 106 may analyze or process such information to develop, update or revise a pre-operation plan or an operation recommendation.

One or more of the data stores 122a-N may store diagnostic information, as discussed in more detail below. One or more of the data stores 122a-N may store inventory information. Inventory information refers to information about a current state of inventory of medical supplies needed to perform one or more medical procedures. For example, spinal implant surgery may require a certain number of spinal implants, and each spinal implant may have one or more components such as, for example, intervertebral implants, plates, pedicle screws and/or anchoring members, rods, etc. An inventory data store 122a-N may store information about the current inventory of these components such as, for example, a part number, a model number, a number of available components, a set or configuration number, an indication of a substitutable component, a reorder status and/or the like.

As illustrated by FIG. 1, a hospital record system 108 may include one or more hospital electronic devices 124a-N and one or more data stores 126a-N, The data stores 126a-N may be used to store medical record information for one or more patients. Medical record information may include, without limitation, electronic medical records (EMRs) and/or electronic health records (EHRs). This information may include images, such as x-ray images, catscan or CT images, radiographs, MRIs and/or the like, associated with patient.

In an embodiment, an operating room system 110 may include one or more operating room electronic devices 128a-N. An operating room electronic device 128a-N may be one that is present in an operating room such as, for example, a tablet or a laptop. An operating room system 110 may also include one or more items of equipment 130. An item of equipment 130 may be configured to communicate with one or more operating room electronic devices 128a-N and/or other electronic devices such as, for example, via a wireless communication channel. Example equipment 30 may include, without limitation, monitoring devices, surgical navigation systems (e.g., Medtronic Stealth Station), robotics systems (e.g., Mazor X Robotic Guidance System), surgical equipment and/or the like. For example, an embodiment of the system may integrate the data obtained in the client system 102 and/or surgeon system 104 with the pre-operative planning software in the Mazor X system software to provide the Mazor system with the information obtained through an embodiment of the system to plan, revise, adjust or otherwise alter, and thereafter conduct a surgical procedure.

As illustrated by FIG. 1, the client system 102, surgeon system 104, analytics system 106, hospital record system 108 and/or an operating room system 110 may communicate with one or more of the other systems via a communication network 112*a*-N. A communication network 112*a*-N may be a local area network (LAN), a wide area network (WAN), a mobile or cellular communication network, an extranet, an intranet, the Internet, a short range communication network and/or the like. Although FIG. 1 shows separate communication networks 112*a*-N, it is to be understood that these networks, or some combination of these networks, may be implemented as a single communication network.

Figure 2:
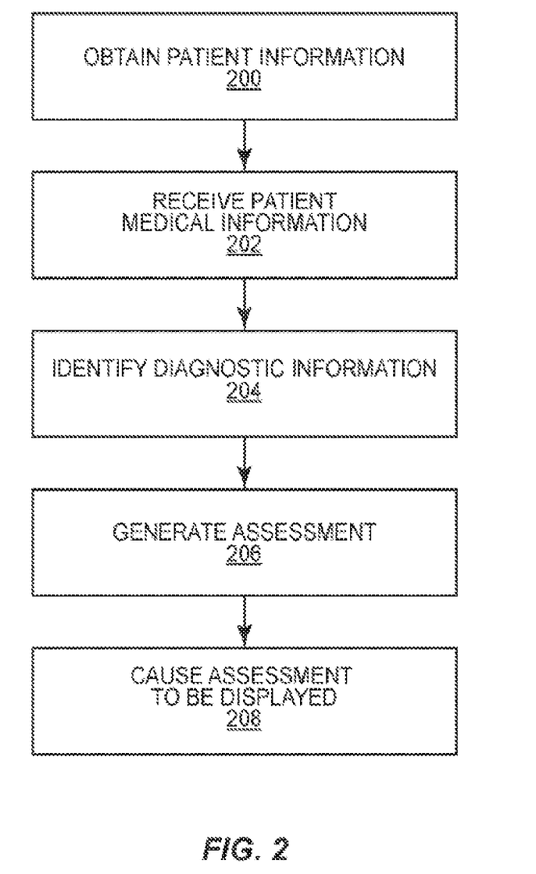
FIG. 2 illustrates an example method of generating a surgical assessment according to an embodiment.

FIG. 2 illustrates an example method of generating a surgical assessment according to an embodiment. As illustrated by FIG. 2, patient information may be obtained 200 by an analytics system. An analytics system may obtain 200 patient information from one or more client electronic devices.

Patient information may include information that a patient provides directly. Patient information may include personal information about the patient, such as name, address, gender, contact information and/or the like. Patient information may also include information about the patient's condition. For instance, a patient may be assessed for spinal surgery, so the patient may provide information pertaining to the patient's back condition, pain level, treatments and/or the like. Patient information may be provided by a patient or with a patient's approval.

In an embodiment, a patient may provide patient information via a client electronic device. A patient may use his or her own client electronic device to provide patient information. For example, a patient may provide patient information via an application resident on or accessible via the patient's client electronic device (such as, for example, a mobile phone or a tablet). Alternatively, a patient may provide patient information via a website that is accessible through a laptop computer, a desktop computer or other electronic device.

Figure 3:
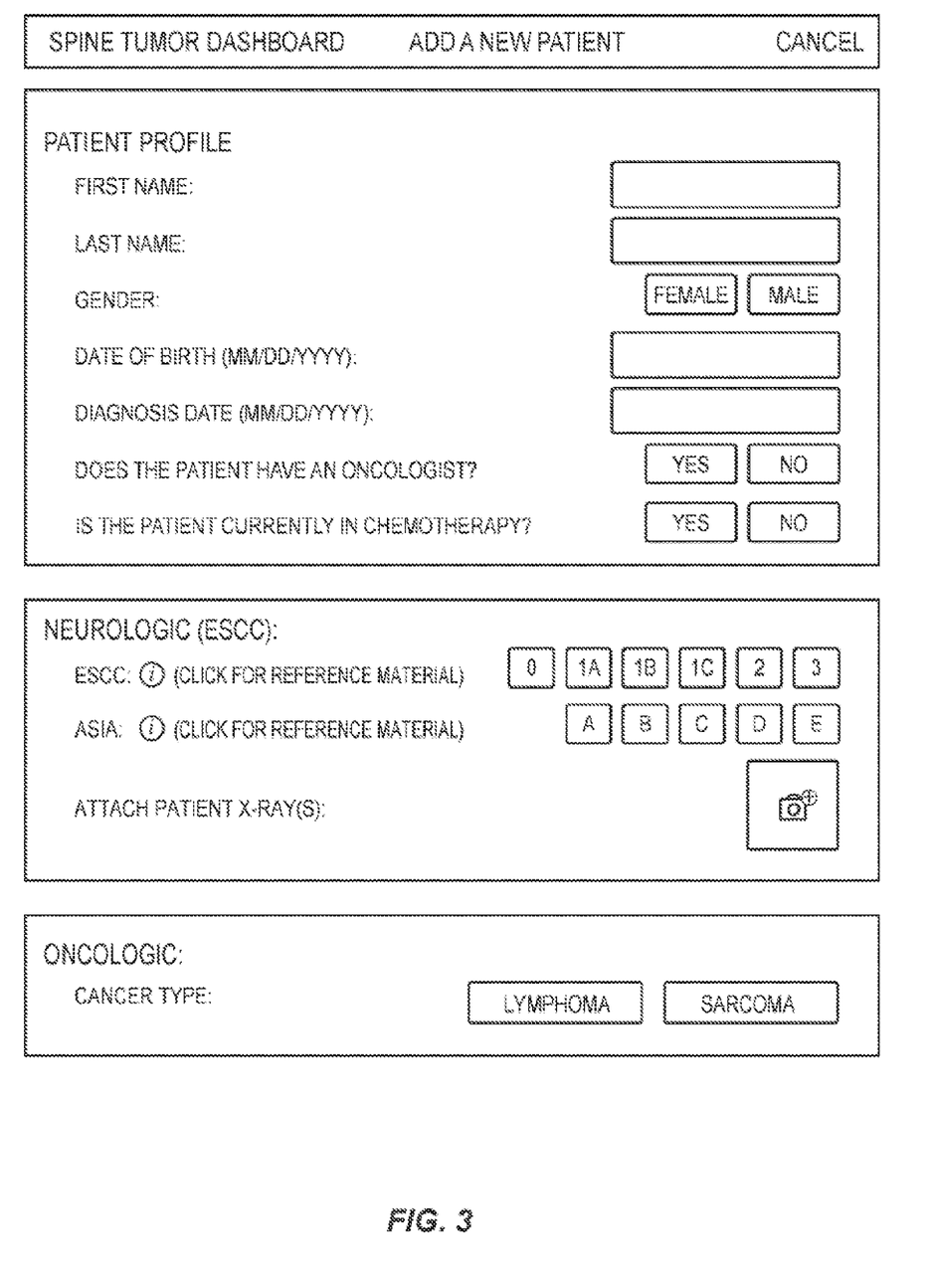
FIG. 3 and FIG. 4 illustrate example graphical user interfaces that a healthcare provider may use to provide patient information according to various embodiments.
Figure 4:
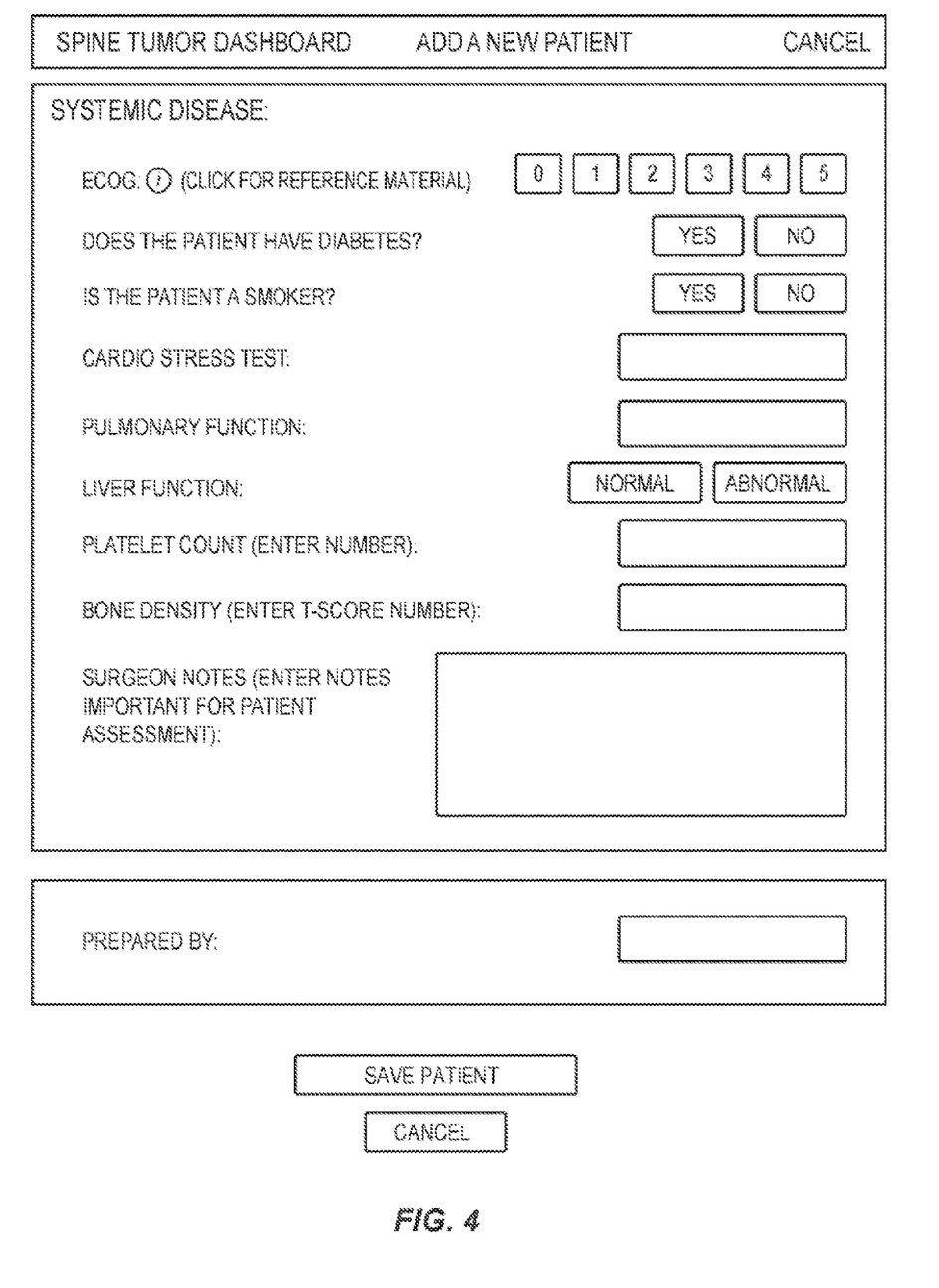

In an embodiment, a patient may provide patient information using a client electronic device that is not associated with or that belongs to the patient. For instance, a patient who is being evaluated in a clinical setting may be provided an electronic device to use to enter patient information. In yet another example, a third party, such as a healthcare provider, may enter patient information via a client electronic device on a patient's behalf. For instance, a surgeon or other healthcare provider may provide information about a patient's condition such as, for example, results of a physical examination. FIG. 3 and FIG. 4 illustrate example graphical user interfaces that a healthcare provider may use to provide patient information according to various embodiments.

Patient information may include information about a patient that is collected by one or more sensors. Sensors may be positioned on an external portion of a patient on or near an area of patient concern. For instance, a patient may wear a patch or other device on a portion of a patient's lower back that has one or more sensors. The sensors may measure certain values associated with the patient's movement, such as, for example, translation about an x, y, or z axis (e.g., pitch, roll and/or yaw), angular velocity, gravity, pressure, acceleration, gyroscopic rotation and/or rotational orientation, direction in motion, heave, surge, sway, position and/or the like. In this regard, the sensor systems disclosed in U.S. patent application Ser. No. 16/039,592 entitled Load Sensing Assembly for a Spinal Implant, herein by reference in their entirety.

As another example, one or more sensors may be located internally. For instance, one or more sensors may be incorporated into an implant, such as a spinal implant. The sensors may obtain one or more measurements and send one or more measurements to an electronic device located externally to a patient via a wireless communication network. For example, a load sensing assembly of a spinal implant may obtain one or more measurements pertaining to a force between a set screw of the implant and a longitudinal member when the set screw is engaged with an anchoring member of an implant. Alternate sensors may be used within the scope of this disclosure. In this regard, the sensor systems disclosed in U.S. patent application Ser. No. 16/039, 592 entitled Load Sensing Assembly for a Spinal Implant, are incorporated herein by reference in their entirety.

In an embodiment, one or more client electronic devices may send at least a portion of patient information to an analytics system.

Referring back to FIG. 2, an analytics system may receive 202 patient medical information. Patient medical information may include information from a patient's medical or health record, such as, for example, electronic medical record (EMR) data or electronic health record (EHR) data. In certain embodiments, patient medical information may include one or more medical images of at least a portion of a patient's body. A medical image may be a CT scan image, an x-ray image, an MRI image and/or the like.

In various embodiments, an analytics system may receive 202 patient medical information from a hospital record system. Alternatively, a client system may receive patient medical information from a hospital record system, and may provide at least a portion of the patient medical information to the analytics system.

An analytics system may perform one or more image processing techniques on a medical image to calculate one or more relevant measurements from the image, such as, for example, dimensional constraints (e.g., length, width, diameter, height, volume, angulation) for screws, rods, plates, or intervertebral implants and/or potential positioning or locational constraints or optimization for individual implants or multiple implants operating in concert and/or used together to correct one or more conditions. Sagittal mobility may further be assessed using images and related data obtained by various embodiments of the system. In addition, lordosis angles and disc heights may be obtained through various images and data that may be obtained in certain embodiments.

An analytics system may store diagnostic information in one or more data stores of the analytics systems, or in one or more data stores that are accessible by the analytics system. Diagnostic information refers to information pertaining to one or more medical conditions, and/or the treatment of one or more medical conditions. In an embodiment, diagnostic information may include medical journals, articles, research studies and/or the like.

In various embodiments, the diagnostic information may be categorized, labeled or tagged according to the medical condition(s) to which such diagnostic information pertains. For instance, a research study pertaining to the efficacy of spinal implants may be categorized, labeled or tagged as pertaining to "spinal conditions." In some embodiments, diagnostic information may pertain to more than one medical condition.

Referring back to FIG. 2, an analytics system may identify 204 at least a portion of relevant diagnostic information. An analytics system may ascertain from at least a portion of the received patient information and/or patient medical information a type of medical condition associated with the patient. For instance, an analytics system may parse at least a portion of the received patient information and/or the received patient medical information for one or more key words that correspond to one or more of the categories, labels or tags associated with the diagnostic information. The analytics system may use the parsed information to identify 204 at least a portion of relevant diagnostic information.

In an embodiment, an analytics system may generate 206 a patient assessment based on at least a portion of the patient information, the patient medical information and/or the relevant diagnostic information. For instance, an analytics system may analyze one or more medical images, or portions thereof, to ascertain information pertaining to a patient's medical condition.

In various embodiments, an assessment may be generated using one or more machine learning techniques or models such as, for example, a support vector machine learning model, logistical regression or neural networks. A machine learning model may be trained on a data set for a desired bodily structure, pathology, condition, classification and/or the like.

For example, a machine learning model may be trained on a data set for a particular pathology. The data set may include images indicative of the pathology and/or images not indicative of the pathology. Similarly, a data set may be trained on a data set for a particular condition such as, for example, a broken bone, the presence of a tumor, the presence of a deformity, the existence of trauma and/or the like. The data set may include one or more images indicative of the condition and/or one or more images not indicative of the condition.

For example, a machine learning model may be used to provide a probability of a patient having stenosis. The model may be trained on labeled images depicting stenosis in other individuals. The model may also be trained on labeled images of other conditions that are not stenosis, such as, for example, spondylolisthesis and disc herniation. The labels may correspond to dimensions, properties or characteristics of various components, such as, for example, foraminal height, cord deformation, lateral recess volume, and/or the like. Through this training, the model may learn features in the labeled images.

When a model is applied to an image, it may generate a probability that a patient is exhibiting a pathology or condition defined by the model. The model may be updated based on feedback received from users of the system. For instance, if a model predicts that it is unlikely that a patient has a particular condition, but the patient is diagnosed by a doctor as having that condition, the model may be updated with this information to further refine the model.

In certain embodiments, an analytics system may use pattern matching to determine whether a similarity exists between at least a portion of a patient medical image and at least a portion of one or more images of a data set. For instance, an analytics system may compare an image of a patient's femur with an image of a broken femur to determine if a similarity exists. A similarity may be determined to exist if a pixel-level analysis of the images results in a match within a certain degree of certainty or within a certain standard deviation. If a similarity exists, the analytics system may generate an assessment that includes an indication that the patient's medical images exhibit characteristics consistent with those associated with a broken femur.

Similarly, a machine learning technique may compare an image of a patient's femur with an image of a non-broken femur of a data set to determine if a similarity exists. If a similarity exists, the analytics system may generate an assessment that includes an indication that the patient's medical images exhibit characteristics consistent with those associated with a non-broken femur.

In various embodiments, an analytics system may retrieve condition-specific medical images from a data store that is a part of the analytics system or that is other accessible by the analytics system such as, for example, via a communication channel.

An obtained medical image may be converted to a format that is compatible with a machine learning technique, and the technique may be applied to the image representation.

In other embodiments, an analytics system may analyze one or more medical images to determine a condition classification. A classification may refer to a specific type of medical condition. For instance, a spinal condition may be associated with a variety of different classifications such as, for example, a lumbar degenerative classification, an anterior-cervical classification, a TL complex degenerative classification, a cervical complex degenerative classification, an adult deformity classification, a pediatric deformity classification, a tumor classification and/or a trauma classification. Additional and/or alternate classifications may be used within the scope of this disclosure.

An analytics system may determine a condition classification by applying a machine learning model that compares at least a portion of one or more of the received patient medical images to at least a portion of one or more images associated with either a known classification or a known lack of classification.

For instance, an analytics system may want to determine whether a patient has experienced spinal trauma. The analytics system may apply a machine learning model that compares at least a portion of the medical images of a patient to at least a portion of the retrieved images to determine whether a similarity exists. In certain embodiments, a machine learning model may use pattern matching to determine whether a similarity exists between at least a portion of a patient medical image and at least a portion of a classification-specific medical image.

In various embodiments, an analytics system may analyze one or more medical images to determine one or more dimensions associated with a particular bodily structure. The dimensions may be relevant to one or more implants that may be needed or recommended to treat a patient's condition. For instance, a patient's spinal condition may be recommended to be treated with a spinal implant, such as a screw assembly and a spinal rod (or other similar types of implants). A spinal rod may be attached to the exterior of two or more vertebral members to assist with the treatment of a spinal disorder. Screw assemblies may be used to connect a longitudinal member to a vertebral member. An analytics system may analyze one or more medical images to of at least a portion of a patient's spine to determine one or more dimensions pertaining to one or more of the patient's vertebral members such as, for example, distance between vertebral members. An analytics system may use one or more of the determined dimensions to recommend one or more implant options, as described in more detail below.

In an embodiment, the type of analysis that an analytics system may perform may be based on input received from a user of the system such as for example, a healthcare provider. For instance, a surgeon may provide input indicating that an analytics system should analyze one or more medical images to determine one or more specific dimensions of a bodily structure.

An assessment may include at least a portion of the patient information, the patient medical information, and/or any relevant medical images. An assessment may also include information pertaining to an analysis performed by an analytics system. For instance, if an analytics system analyzed one or more medical images to determine if a certain condition exists, the assessment may include an indication of whether the system determined that the conditioned exists or not. As another example, if the analytics system analyzed one or more medical images to determine a classification associated with a condition, the assessment may include an indication of the classification determined by the system. As yet another example, if the analytics system analyzed one or more medical images to determine one or more dimensions of a portion of interest of a patient, the assessment may include one or more of the dimensions.

In various embodiments, an assessment may include a diagnosis of a medical condition for a patient, the potential for complications, and/or an indication of whether surgery is recommended for the patient. However, in such situations, the recommendations can preferably be confirmed by a licensed medical professional before they are implemented.

In various embodiments, if an analytics system obtained one or more dimensions pertaining to an area of a patient's body, the analytics system may use one or more of the dimensions to determine one or more medical supplies for a procedure. For instance, an analytics system may determine one or more implants or implant components that may be options for the patient based on the obtained dimensions.

In an embodiment, an analytics system may cross reference at least a portion of obtained dimensions with information from a component data store. A component data store may store information pertaining to one or more medical supplies, such as, for example, lengths, widths, diameters, trajectories, weights, volumes, compositions and/or other dimensional information for one or more supplies or components of one or more supplies. In various embodiments, a component data store may also store a unique identifier associated with one or more supplies. A component data store may be implemented as part of an inventory data store, as discussed below, or as a separate data store.

In various embodiments, an analytics system may compare at least a portion of obtained dimensions with one or more dimensions included in a component data store to identify one or more medical supplies that may be used. For instance, an analytics system may determine that a spinal rod having a length of x cm is required for a patient based on a distance between two of the patient's vertebral members. The analytics system may search the component data store for spinal implants having spinal rod components with a length of x cm and include an indication of such spinal implants in an assessment for the patient. Additional and/or alternate components, supplies, measurements and dimensions may be used within the scope of this disclosure.

In an embodiment, an assessment system may analyze the current inventory to determine whether any medical supplies need to be ordered to perform a procedure. For instance, an analytics system may include or have access to one or more data stores that store information about what medical supplies are needed for one or more medical procedures. This information may include descriptions of the supplies, unique identifiers associated with the supplies, a number of required supplies for a procedure and/or the like. The analytics system may use the diagnosis from the generated assessment to identify the specific procedure at issue. The analytics system may use the identified procedure to identify one or more supplies that are needed to perform the procedure.

In an embodiment, the analytics system may cross reference the identified supplies with an inventory data store. For instance, the analytics system may cross reference a unique identifier obtained from a component data store with an inventory data store to determine whether a particular medical supply or component is stocked or not. An inventory data store may store inventory information about medical supplies. This information may include, without limitation, the number of each type of supply that is available or stocked, a unique identifier associated with the supply, location of the supply, and/or the like.

If the analytics system determines that all of the identified supplies are in stock, the analytics system may include this information in its generated assessment. The analytics system may also include information about the supplies, such as, for example, unique identifiers or location. Alternatively, if the analytics system determines that one or more of the identified supplies is not currently in stock, the analytics system may include an indication in the assessment of which supplies will need to be reordered. The analytics system may automatically initiate a re-order of any such supplies by, for example, sending a request to an inventory management system.

In various embodiments, a generated assessment may include an indication of one or more medical supplies or components that are recommended for a procedure. The assessment may also include an indication of whether the particular supply or component is currently stocked or not.

Referring back to FIG. 2, an analytics system may cause 208 at least a portion of a generated assessment to be displayed at one or more client electronic devices and/or surgeon electronic devices. For instance, a surgeon who access a patient's records may be able to access and view the assessment from the surgeon's electronic device. As another example, a patient may be able to access and view his or her own assessment using his or her own electronic device.

Figure 5:
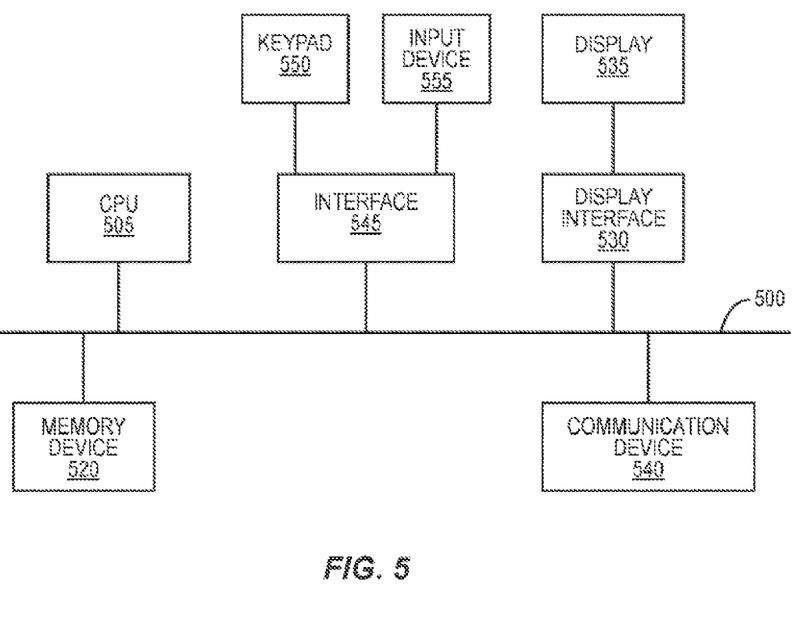
FIG. 5 depicts a block diagram of an example of internal hardware that may be used to contain or implement program instructions according to an embodiment.

FIG. 5 illustrates example hardware that may be used to contain or implement program instructions. A bus 500 serves as the main information highway interconnecting the other illustrated components of the hardware. CPU 505 is the central processing unit of the system, performing calculations and logic operations required to execute a program. CPU 505, alone or in conjunction with one or more of the other elements disclosed in FIG. 5, is an example of a processor as such term is used within this disclosure. Read only memory (ROM) and random access memory (RAM) constitute examples of non-transitory computer-readable storage media 520, memory devices or data stores as such terms are used within this disclosure.

Program instructions, software or interactive modules for providing the interface and performing any querying or analysis associated with one or more data sets may be stored in the memory device 520. Optionally, the program instructions may be stored on a tangible, non-transitory computer-readable medium such as a compact disk, a digital disk, flash memory, a memory card, a USB drive, an optical disc storage medium and/or other recording medium.

An optional display interface 530 may permit information from the bus 500 to be displayed on the display 535 in audio, visual, graphic or alphanumeric format. Communication with external devices may occur using various communication ports 540. A communication port 540 may be attached to a communications network, such as the Internet or an intranet.

The hardware may also include an interface 545 which allows for receipt of data from input devices such as a keypad 550 or other input device 555 such as a touch screen, a remote control, a pointing device, a video input device and/or an audio input device.

It will be appreciated that the various above-disclosed and other features and functions, or alternatives thereof, may be desirably combined into many other different systems or applications or combinations of systems and applications. Also that various presently unforeseen or unanticipated alternatives, modifications, variations or improvements therein may be subsequently made by those skilled in the art which are also intended to be encompassed by the following claims.

What is claimed is:

1. A system comprising:
one or more computing devices and a computer-readable storage medium, wherein the computer-readable storage medium comprises one or more programming instructions that, when executed, cause the one or more computing devices to:
receive a plurality of pieces of diagnostic information, each piece of diagnostic information categorized as pertaining to one or more corresponding specific types of spinal condition;
receive patient information pertaining to a patient;
analyze the patient information to ascertain a specific type of spinal condition associated with the patient;
generate an assessment for the patient and the ascertained specific type of spinal condition by:
identifying, based on the ascertained specific type of spinal condition, a portion of the plurality of pieces of diagnostic information comprising pieces of diagnostic information that are categorized as pertaining to the ascertained specific type of spinal condition;
training a machine learning model on a data set comprising the identified diagnostic information categorized as pertaining to for the ascertained specific type of spinal condition to produce a trained machine learning model capable of recognizing the ascertained specific type of spinal condition in a medical image and determining a probability of the patient having the ascertained specific type of spinal condition, wherein the data set comprises one or more images depicting the ascertained specific type of spinal condition and one or more images that do not depict the ascertained specific type of spinal condition;
receiving medical records associated with the patient, the medical records comprising one or more medical images associated with the patient; and
applying the trained machine learning model to at least a portion of one or more of the received medical images to generate the assessment that the patient exhibits the specific type of spinal condition;
receive information about components for treating the specific type of spinal condition exhibited by the patient;
based on the received information, identify one or more implant components for treating the spinal condition of the patient by searching a component data store;
determine whether the one or more implant components are currently stocked; and
on a condition that the one or more implant components are determined to be out of stock, generate and place an order for the one or more implant components.

2. The system of claim 1, wherein the trained machine learning model is further trained based on whether the patient actually exhibits the specific type of spinal condition.

3. The system of claim 1, wherein the one or more programming instructions further cause the one or more computing devices to identify, based one or more of the received medical images, one or more dimensional constraints pertaining to the implant components, wherein the one or more programming instructions that cause the one or more computing devices to identify the one or more implant components for treating the spinal condition of the patient comprise instructions that cause the one or more computing devices to search the component data store for one or more implant components having dimensions that corresponds to the one or more dimensional constraints.

4. The system of claim 3, wherein the one or more programming instructions that cause the one or more computing devices to identify the one or more dimensional constraints pertaining to the implant components comprise instructions that cause the one or more computing devices to apply a machine learning model that has been trained on a set of bodily structures.

5. The system of claim 3, wherein the one or more programming instructions that cause the one or more computing devices to identify the one or more implant components for the patient comprise instructions that cause the one or more computing devices to identify a unique identifier associated with each implant component having dimensional information that corresponds to the one or more dimensional constraints.

6. The system of claim 5, wherein the one or more programming instructions that cause the one or more computing devices to determine whether the one or more implant components are currently stocked comprise instructions that cause the one or more computing devices to:
search an inventory data store for one or more of the unique identifiers; and
determine an inventory status associated with the one or more unique identifiers.

7. The system of claim 3, wherein the one or more dimensional constraints comprise a length, width, diameter, or height of the implant components.

8. The system of claim 3, wherein the implant components comprise screws, rods, or plates.

9. The system of claim 1, wherein the one or more programming instructions that cause the one or more computing devices to receive the one or more medical images associated with the patient comprise instructions that cause the one or more computing devices to receive the one or more medical images from one or more of the following:
electronic medical record data; or
electronic health record data.

10. The system of claim 1, wherein the one or more programming instructions further cause the one or more computing devices to:
on a condition that the one or more implant components are determined to be in stock, generate a supply assessment comprising location information of one or more of the implant components.

11. The system of claim 10, wherein the one or more programming instructions further cause the one or more computing devices to cause the supply assessment to be displayed on a display device of a client electronic device.

12. The system of claim 1, wherein the one or more programming instructions that cause the one or more computing devices to receive the patient information comprise instructions that cause the one or more computing devices to receive information about the patient that is collected by one or more sensors that are internal to the patient.

13. The system of claim 1, wherein the one or more programming instructions that cause the one or more computing devices to analyze the patient information comprise instructions that cause the one or more computing devices to parse at least the portion of the received patient information for one or more key words that correspond to the specific type of spinal condition.

14. The system of claim 1, wherein the one or more programming instructions that cause the one or more computing devices to analyze the patient information comprise instructions that cause the one or more computing devices to analyze at least the portion of the one or more medical images to determine the specific type of spinal condition.

15. The system of claim 1, wherein the one or more programming instructions that cause the one or more computing devices to apply the trained machine learning model to at least the portion of one or more of the received medical images to generate the assessment that the patient exhibits the specific type of spinal condition comprise instructions that cause the one or more computing devices to apply the trained machine learning model to at least the portion of one or more of the received medical images to generate a probability that the patient exhibits the specific type of spinal condition.

16. The system of claim 1, wherein the one or more programming instructions further cause the one or more computing devices to cause the generated assessment to be displayed on a display of a client electronic device.

* * * * *